United States Patent
Knauf et al.

(10) Patent No.: US 9,840,461 B2
(45) Date of Patent: Dec. 12, 2017

(54) METHOD FOR OPERATING A GAS-PHASE PHOSGENATION PLANT

(71) Applicant: Covestro Deutschland AG, Leverkusen (DE)

(72) Inventors: Thomas Knauf, Dormagen (DE); Wolfgang Lorenz, Dormagen (DE); Friedhelm Steffens, Leverkusen (DE); Rainer Bruns, Bergisch Gladbach (DE); Wolfgang Taube, Neuss (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 15/128,179

(22) PCT Filed: Mar. 24, 2015

(86) PCT No.: PCT/EP2015/056214
§ 371 (c)(1),
(2) Date: Sep. 22, 2016

(87) PCT Pub. No.: WO2015/144681
PCT Pub. Date: Oct. 1, 2015

(65) Prior Publication Data
US 2017/0101367 A1    Apr. 13, 2017

(30) Foreign Application Priority Data
Mar. 27, 2014   (EP) ..................................... 14162004

(51) Int. Cl.
| C07C 263/00 | (2006.01) |
| C07C 263/10 | (2006.01) |
| C07C 263/20 | (2006.01) |
| C01B 31/28  | (2006.01) |
| B01J 12/00  | (2006.01) |

(52) U.S. Cl.
CPC .......... C07C 263/10 (2013.01); B01J 12/005 (2013.01); C01B 31/28 (2013.01); C07C 263/20 (2013.01)

(58) Field of Classification Search
CPC ... C07C 263/10; C07C 263/02; C07C 263/20; B01J 12/005; C01B 31/28
See application file for complete search history.

(56) References Cited

U.S. PATENT DOCUMENTS

| 4,847,408 A | 7/1989 | Frosch et al. |
| 5,679,839 A | 10/1997 | Armand et al. |
| 7,084,297 B2 | 8/2006 | Woelfert et al. |
| 7,754,915 B2 | 7/2010 | Herold et al. |
| 7,915,444 B2 | 3/2011 | Woelfert et al. |
| 8,173,833 B2 | 5/2012 | Woelfert et al. |
| 8,258,337 B2 | 9/2012 | Woelfert et al. |
| 8,399,702 B2 | 3/2013 | Pohl et al. |
| 8,563,768 B2 | 10/2013 | Bruns et al. |
| 8,692,016 B2 | 4/2014 | Sanders et al. |
| 8,779,181 B2 | 7/2014 | Mattke et al. |
| 9,006,481 B2 | 4/2015 | Mattke et al. |
| 9,302,983 B2 | 4/2016 | Lehr et al. |
| 2010/0041915 A1 | 2/2010 | Woelfert et al. |
| 2010/0123152 A1* | 5/2010 | Sugisawa ............ H01L 51/5052 257/98 |
| 2011/0301380 A1* | 12/2011 | Knoesche ............. C07C 263/10 560/347 |
| 2015/0291512 A1 | 10/2015 | Burns et al. |
| 2015/0368190 A1 | 12/2015 | Steffens et al. |

FOREIGN PATENT DOCUMENTS

| EP | 1371635 A1 | 12/2003 |
| EP | 1371636 A1 | 12/2003 |
| EP | 1413571 A1 | 4/2004 |
| WO | 2013029918 A1 | 3/2013 |
| WO | WO2013029918 | * 3/2013 |

OTHER PUBLICATIONS 918 translated 8 pages 2013.*
WO2013029918 translated 2013.*

* cited by examiner

Primary Examiner — Yevegeny Valenrod
Assistant Examiner — Blaine G Doletski
(74) Attorney, Agent, or Firm — N. Denise Brown

(57) ABSTRACT

This invention relates to a process for operating a gas phase phosgenation plant (100) to form an isocyanate (4) by reacting an amine (2) with phosgene (1), in which the gas phase phosgenation plant is started up by first charging the plant with phosgene. At the same time as, or after the first charge of phosgene, the amine supply devices are rendered inert using a hot inert gas stream (30). Then, amine is admixed for the first time. In this way and by maintaining a pressure drop in the amine and phosgene devices to the mixing zone, the back mixing of phosgene into the amine-containing reactant stream during start-up is prevented.

16 Claims, 3 Drawing Sheets

METHOD FOR OPERATING A GAS-PHASE PHOSGENATION PLANT

CROSS-REFERENCE TO RELATED APPLICATIONS

This application is a National Phase Application of PCT/EP2015/056214, filed Mar. 24, 2015, which claims priority to European Application No. 14162004.7, filed Mar. 27, 2014, each of which being incorporated herein by reference.

FIELD

The invention relates to a method of operating a gas phase phosgenation plant (100) for reacting an amine (2) with phosgene (1) to give the corresponding isocyanate (4), in which the gas phase phosgenation plant (100) is started up by first charging it with phosgene. Simultaneously with or after the first charge with phosgene, the amine feed devices are inertized with the aid of a hot inert gas stream (30). Only thereafter is amine added for the first time. These measures and observation of a pressure gradient over the amine and phosgene feed devices toward the mixing zone prevent backmixing of phosgene into the amine-containing reactant stream during the startup.

BACKGROUND

Isocyanates are produced in large volumes and serve mainly as starting materials for production of polyurethanes. They are usually prepared by reacting the corresponding amines with phosgene, using phosgene in a stoichiometric excess. The reaction of the amines with the phosgene can be effected either in the gas phase or in the liquid phase. It is a feature of the process regime in the gas phase, typically referred to as gas phase phosgenation, that the reaction conditions are chosen such that at least the amine, isocyanate and phosgene reaction components, but preferably all the reactants, products and reaction intermediates, are gaseous under the conditions chosen. Advantages of gas phase phosgenation include reduced occurrence of phosgene (called phosgene "hold-up"), the avoidance of intermediates that are difficult to phosgenate, increased reaction yields and a lower energy requirement, since less solvent is being employed. The present invention relates exclusively to gas phase phosgenation and relates especially to a seamless method of starting up a gas phase phosgenation plant.

The prior art discloses various processes for preparing isocyanates by reacting amines with phosgene in the gas phase. An important factor for a good process regime is good mixing of the reactants of the gas phase phosgenation. EP-A-0 289 840 describes the preparation of diisocyanates by gas phase phosgenation, wherein the preparation in accordance with the invention takes place in a turbulent flow at temperatures between 200° C. and 600° C. in a cylindrical space without moving parts.

EP-A-0 570 799 relates to a process for preparing aromatic diisocyanates, in which the reaction of the corresponding amine with the phosgene is conducted in a tubular reactor above the boiling temperature of the diamine within a mean contact time of 0.5 to 5 seconds.

EP-A-0 699 657 describes a process for preparing aromatic diisocyanates in the gas phase, in which the reaction of the corresponding diamine with the phosgene takes place in a reactor comprising two zones, wherein the first zone, which makes up about 20% to 80% of the total reactor volume, has ideal mixing and the second zone, which makes up 80% to 20% of the total reactor volume, can be characterized by plug flow. Preferably, the second reaction zone is executed as a tubular reactor.

The optimization of the use of tubular reactors for gas phase phosgenation, the principle of which has been disclosed in EP-A-0 570 799 with use of the jet mixer principle (Chemie-Ing.-Techn. 44 (1972) p. 1055, FIG. 10), is the subject of numerous applications.

According to the teaching of EP-A-1 362 847, homogenization of the reactant stream supplied via the ring space of the tubular reactor and very central feeding of the two reactant streams into the tubular reactor have a great positive influence on the stability of the reaction zone and hence on the gas phase reaction overall.

As described in EP-A-1 555 258, enlargement of the tubular reactor used also necessitates enlargement of the mixing nozzle, which frequently takes the form of a smooth jet nozzle. However, the increase in the diameter of the smooth jet nozzle also reduces the speed of mixing of the central jet as a result of the greater diffusion length required and increases the risk of backmixing, which in turn leads to the formation of polymeric impurities and hence of solid material baked onto the reactor. According to the teaching of EP-A-1 555 258, the disadvantages described can be eliminated when one reactant stream is injected at high velocity via a concentric annular gap in the stream of the other reactant. This makes the diffusion length for mixing small and the mixing times very short. The reaction can then proceed with high selectivity to give the desired isocyanate. The occurrence of polymeric impurities and the formation of caked-on material are reduced thereby.

According to the teaching of EP-A-1 526 129, an increase in the turbulence of the reactant stream in the central nozzle has a positive influence on the mixing of the reactants and hence on the gas phase reaction overall. As a result of the better mixing, there is a decrease in the tendency to form by-products.

EP-A-1 449 826 discloses a process for preparing diisocyanates by phosgenation of the corresponding diamines, in which the vaporous diamines, optionally diluted with an inert gas or with the vapors of an inert solvent, and phosgene, are heated separately to temperatures of 200° C. to 600° C. and mixed and reacted in a tubular reactor, wherein a number n≥2 of nozzles aligned parallel to the axis of the tubular reactor are arranged within the tubular reactor, wherein the stream comprising the diamines is fed to the tubular reactor via the n nozzles and the phosgene stream is fed to the tubular reactor via the remaining free space.

A further development of the use of tubular reactors for gas phase phosgenation is the subject of WO 2007/028715. The reactant used has a mixing device and a reaction space. According to the teaching of WO 2007/028715, the reaction space comprises, in the front region, the mixing space in which predominantly the mixing of the gaseous phosgene and amine reactants, optionally mixed with inert medium, takes place, which is generally accompanied by the onset of the reaction. According to the teaching of WO 2007/028715, in the rear part of the reaction space, it is essentially only the reaction that then takes place, and mixing at most to a minor degree. Preferably, in the process disclosed in WO 2007/028715, reaction spaces that are rotationally symmetric with respect to the flow direction are used, it being possible to divide these, in terms of construction, essentially into up to four longitudinal sections along the longitudinal axis of the reactor over the flow profile, the longitudinal sections differing in terms of the size of the cross-sectional flow area.

WO 2008/055898 discloses a process for preparing isocyanates by phosgenation of the corresponding amines in the gas phase in a reactor, in which, analogously to WO 2007/028715, the reactor used has a mixing device and a reaction space, the rotationally symmetric reaction space can be divided, in terms of construction, essentially into up to four longitudinal sections along the longitudinal axis of the reactor over the flow profile, the longitudinal sections differing in terms of the size of the cross-sectional flow area. Compared to WO 2007/028715, the changes in the cross-sectional flow areas, however, are achieved not by means of a voluminous body installed into a tubular reactor but by means of a corresponding extension or constriction of the outer reactor wall.

EP-A-1 275 639 likewise discloses, as a possible process variant for preparation of isocyanates by phosgenation of the corresponding amines with phosgene in the gas phase, the use of a reactor in which the reaction space has, in flow direction, beyond the mixing of the two reactants, an extension of the cross-sectional flow area. By means of a suitably chosen extension of the cross-sectional area, it is possible to keep the flow rate of the reaction mixture over the length of the reactor just constant. This increases the reaction time available with the same reactor length.

EP-A-2 196 455 discloses that phosgene and the primary aromatic amines are converted above the boiling temperature of the amines in a reactor comprising a reaction space which is essentially rotationally symmetric with respect to the flow direction, wherein the cross-sectional average flow rate of the reaction mixture along the axis of the essentially rotationally symmetric reaction space in the section of the reaction space in which the conversion of the amino groups to the isocyanate groups is between 4% and 80% is not more than 8 m/sec and wherein the cross-sectional average flow rate of the reaction mixture along the axis of the essentially rotationally symmetric reaction space in this section of the reaction space is always below the cross-sectional average flow rate at the start of this section.

EP-A-1 935 876 discloses a gas phase process for preparing isocyanates by reacting corresponding primary amines with phosgene, in which phosgene and the primary amines are converted above the boiling temperature of the amines within a mean contact time of 0.05 to 15 seconds, the conversion being conducted adiabatically.

EP-A-2 408 738 discloses how a dissociation of phosgene to chlorine and carbon monoxide as a result of an excessively long residence time of the phosgene-containing streams at high temperature can be avoided. By reduction of the residence time of the phosgene at temperatures greater than 300° C. to a maximum of 5 s and by the limitation of the temperature of the heat transfer areas in contact with phosgene of not more than 20 K above the phosgene temperature to be established, this is said to be avoided.

EP-B-1 935 875 discloses a process for preparing isocyanates by reacting corresponding primary amines with phosgene in the gas phase, in which the reaction is stopped by conducting the reaction mixture out of the reaction space through a cooling zone into which liquids are injected, the direct cooling in the cooling zone being effected in one stage in two or more cooling zones connected in series (called "quenching" of the reaction mixture).

WO 2013/029918 describes a process for preparing isocyanates by reacting the corresponding amines with phosgene, which can also be conducted at different loads on the gas phase plant without any problems, and more particularly, even when running the plant in the partial load range, the mixing and/or the reaction is said to proceed within the optimized residence time window in each case, by increasing the ratio of phosgene to amine or adding one or more inert substances to the phosgene and/or amine stream. The method of the invention is to enable operation of an existing plant at different loads with constant product and process quality. This is to dispense with the provision of several plants with different nameplate capacities.

The application teaches that essential parameters of a phosgenation, such as the residence times of the co-reactants in the individual apparatuses in particular, are optimized for the operation of the production plant at nameplate capacity, which can lead to problems in terms of yield and product purity when the plant is operated at lower than nameplate capacity (cf. page 2 lines 20 to 36). In order to be able to attain the optimized—narrow—residence time window even at partial load (i.e. reduced amine flow rate compared to operation at nameplate capacity), it is suggested that either the phosgene stream and/or the inert fraction be increased (cf. page 3 lines 5 to 19), preferably in such a way that the total flow rate of all components corresponds essentially to that at nameplate capacity (cf. page 6 lines 4 to 8). The application does mention startup operations in the description of the background of the invention claimed on page 2, but does not disclose any technical teaching at all as to the specific way in which a production plant not in operation (i.e. amine flow rate and phosgene flow rate are equal to zero) is most advantageously brought to the desired operating state of the nameplate capacity. The technical measures disclosed in the application (i.e. the increase in the phosgene flow rate and/or the inert fraction) should be considered exclusively in the context of the problem of operation (i.e. the amine flow rate is significantly greater than zero) of a production plant at lower than nameplate capacity, and with the problem of how a plant operated at nameplate capacity can advantageously be switched to operation at lower than nameplate capacity (see the examples).

Although the prior art processes described succeed in conducting a phosgenation without loss of quality in the end products, the only processes described, with a few exceptions, are those in the normal state of operation. There is no description of the startup operation until attainment of a steady operating state at the desired mass flow rate of amine to be converted, i.e. the startup of a gas phase phosgenation plant.

The person skilled in the art is aware that a continuously operated industrial process, proceeding from a production plant not in operation (for example after a maintenance-related shutdown), cannot be run up instantly back to the process parameters prior to the production shutdown. Reactants and apparatuses have to be heated up, apparatuses may have to be inertized, and the loading of the apparatuses with the reactants is gradually increased to the desired target value. The startup of a gas phase phosgenation plant is a frequent everyday industrial operation which need not necessarily be combined with opening or another mechanical intervention into the phosgenation plant. In practice, it is a feature of startup that there may be deviations in the excess of phosgene relative to amine compared to the continuous operation at nameplate capacity of the production plant. Such deviations occur particularly when, for example, pressure variations result in backmixing. This is observed especially when the current flow rate of amine to be converted is very small compared to the target flow rate of amine to be converted at nameplate capacity of the plant. These quantitative variations in the ratio of phosgene to amine are disadvantageous since solids such as polyurea or amine hydrochlorides can precipitate out. Furthermore, in the event of improper startup, there can be unwanted formation of droplets of amine. The startup of a gas phase phosgenation plant is therefore a critical process step, since errors here can seriously disrupt the actual continuous production (for example as a result of an increase in the pressure differential needed to assure a sufficient flow rate of the reactants and products through the plant).

SUMMARY

In spite of the various advances in the field of gas phase phosgenation, there was therefore a need for further improvements. Taking account of this need, the present invention provides a method of operating a gas phase phosgenation plant (100) for reacting an amine (2) with phosgene (1) to give the corresponding isocyanate (4), said gas phase phosgenation plant (100) comprising at least
(i) an apparatus 1000 for providing a gaseous phosgene stream (10), optionally comprising, as well as phosgene (1), an inert substance (3),
(ii) an apparatus 2000 for providing a gaseous amine stream (20), optionally comprising, as well as amine (2), an inert substance (3),
(iii) a mixing zone (3100) for mixing the streams 10 and 20, the mixing zone being connected by each of devices (1100, 2100) to the apparatus 1000 and the apparatus 2000,
(iv) a reaction zone (3200) arranged downstream of the mixing zone (3100) for further conversion of the previously mixed streams 10 and 20,
(v) a reaction stopping zone (4000) arranged downstream of the reaction zone (3200) to end the reaction,
and optionally
(vi) a workup section (5000) comprising devices for recovery and recycling of unconverted phosgene (1") (5100) and devices for obtaining the isocyanate prepared in pure form (5200),
in which, in the regular operation of the gas phase phosgenation plant (100), the phosgene (1) in the phosgene gas stream (10) is preferably a mixture of fresh phosgene (1') and the devices (5100) recovered recycled phosgene (1"), wherein the gas phase phosgenation plant (100) is started up by running the following steps:
(I) providing a gaseous phosgene stream (10) at a temperature $T_{10}$ of 200° C. to 600° C., preferably 200° C. to 500° C. and more preferably 250° C. to 500° C., with an absolute pressure $p_1$ of 100 mbar to 3000 mbar, preferably 150 mbar to 2800 mbar and more preferably 200 mbar to 2500 mbar, in the apparatus 1000 and continuously introducing this gaseous phosgene stream (10) through the device 1100 into the mixing zone (3100), the reaction zone (3200) and the reaction stopping zone (4000), the pressure $p_{10}$ being greater than the pressure $p_{3100}$ in the mixing zone (3100);
(II) simultaneously with or after step (I),
  (a) introducing an inert substance (3), preferably one which is liquid at room temperature and standard pressure, at a temperature $T_3 < 200°$ C. into the apparatus 2000, heating the inert substance (3) in the apparatus 2000 to obtain an inert gas stream (30) which is passed through the device 2100, the mixing zone (3100), the reaction zone (3200) and the reaction stopping zone (4000) or
  (b) introducing an inert gas stream (30)
    (b.1) into the device 2100 and thence through the mixing zone (3100), the reaction zone (3200) and the reaction stopping zone (4000)
    or preferably
    (b.2) into the apparatus 2000 and thence through the device 2100, the mixing zone (3100), the reaction zone (3200) and the reaction stopping zone (4000),
  where the inert gas stream (30) in variant (a) and in variant (b) has a temperature $T_{30}$ of 200° C. to 600° C., preferably 200° C. to 500° C. and more preferably 250° C. to 500° C., and an absolute pressure $p_{30}$ of 100 mbar to 3000 mbar, preferably 150 mbar to 2800 mbar and more preferably 200 mbar to 2500 mbar, the pressure $p_{30}$ in both cases being greater than the pressure $p_{3100}$ in the mixing zone (3100);
(III) after step (II), providing a gaseous amine stream (20) at a temperature $T_{20}$ of 200° C. to 600° C., preferably 200° C. to 500° C. and more preferably 250° C. to 500° C., with an absolute pressure $p_{20}$ of 100 mbar to 3000 mbar, preferably 150 mbar to 2800 mbar and more preferably 200 mbar to 2500 mbar, in the apparatus 2000 and continuously introducing this gaseous amine stream (20) through the device 2100 into the mixing zone (3100), where the pressure $p_{20}$ is greater than the pressure $p_{3100}$ in the mixing zone (3100), and where the composition and the mass flow rate of the stream (20) are matched to the composition and the mass flow rate of stream (10) such that, in the mixing zone (3100), phosgene (1) is present in a stoichiometric excess in relation to the primary amino groups of the amine (2).

DETAILED DESCRIPTION

A gas phase phosgenation is understood in accordance with the invention to mean a process regime for phosgenation of amines to the corresponding isocyanates in which the amines in the gaseous state react to give the isocyanates and, in the course of the reaction, all the components present (reactants, products, intermediates, any by-products, any inert substances) remain in the gas phase during passage through the reaction zone to an extent of at least 95.0% by mass, preferably to an extent of at least 98.0% by mass, more preferably to an extent of at least 99.0% by mass, even more preferably to an extent of at least 99.8% by mass and especially to an extent of at least 99.9% by mass, based in each case on the total mass of all the components present.

Suitable amines (2) are especially isophoronediamine, hexamethylenediamine, bis(p-aminocyclohexyl)methane, tolylenediamine and diphenylmethanediamine. In the context of the present invention, the expression "startup of a gas phase phosgenation plant" encompasses all the process steps required to bring a non-operational gas phase phosgenation plant (for example after a maintenance-related shutdown) to the desired production capacity, expressed as the desired mass flow rate of amine to be converted, $M'_{target}(2)$ [e.g. t(amine)/h]. The operation of the gas phase production plant (100) at $M'_{target}(2)$ is referred to in the context of this invention as regular operation. $M'_{target}(2)$ can, but need not, correspond to the value of $M'_{target}(2)$ at nameplate capacity $M'_{nameplate}(2)$ of the gas phase production plant (100). The nameplate capacity of a production plant is reported in the specialist field as tonnes of product to be produced per year ("tonnes per annum"), taking account of all planned plant shutdowns.

The word "a" in the context of this invention, in connection with countable parameters, should be understood merely as the indefinite article and only as the number "one" when this is stated explicitly, for instance by the addition "exactly one". For example, the expression "a reaction zone" does not rule out the possibility of the presence of two or more reaction zones (connected in series or parallel).

It is essential to the invention that the phosgenation plant (100) is started up by first charging it with phosgene. In the startup operation, the amine is always added after the phosgene, which prevents backmixing of amine into the phosgene pathway and assures an excess of phosgene over amine. Before and preferably also in the course of conversion of the amine to the gas phase, an inert substance is additionally introduced, in order to prevent backflow of phosgene into the amine feed (backmixing) on commencement of amine supply.

The steps of the invention are elucidated in detail hereinafter. Various embodiments can be combined here with one another as desired, unless the opposite is apparent to the person skilled in the art from the context.

Figure 1:
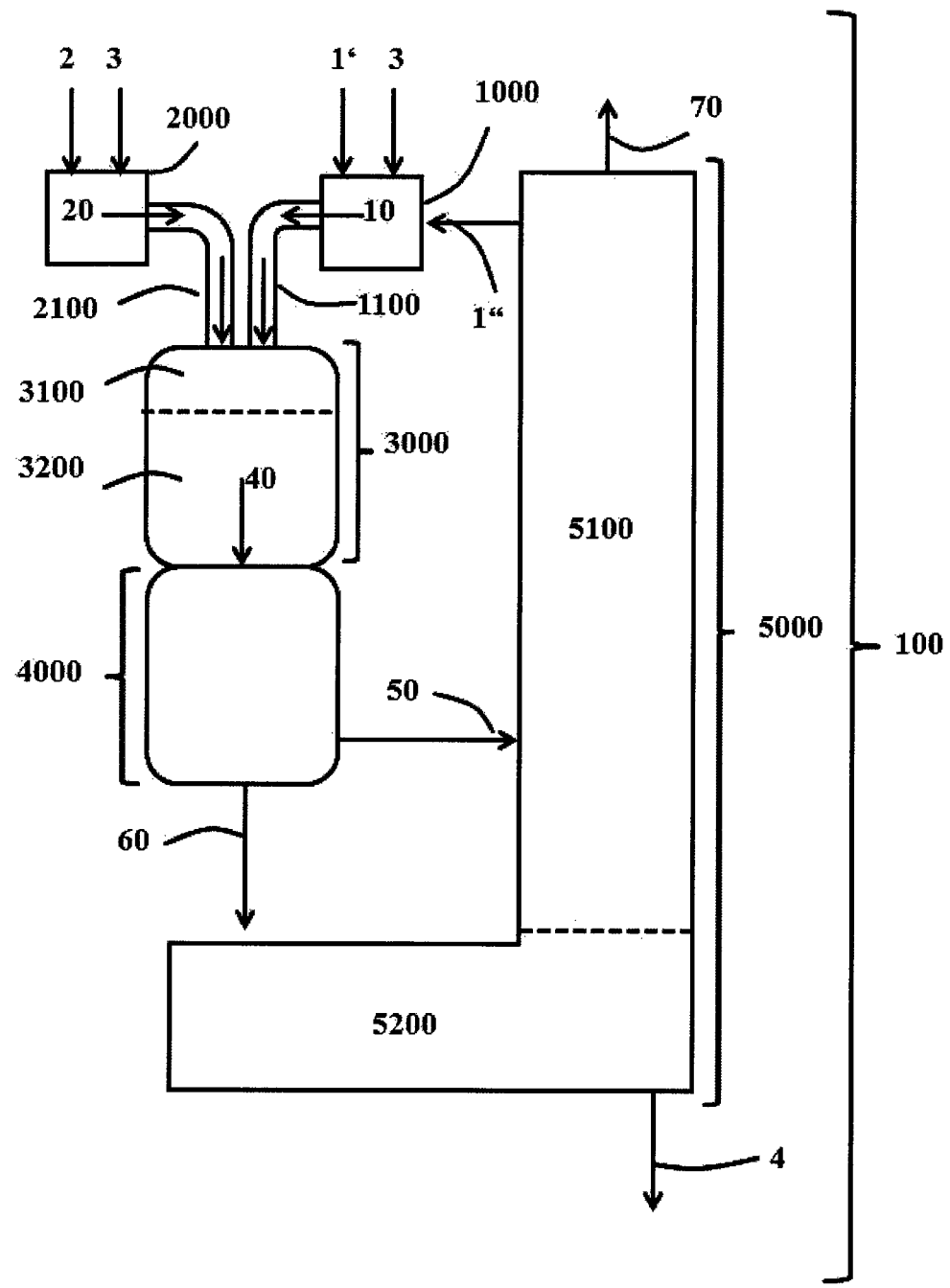
FIG. 1 shows the overall concept of the normal operation of a gas phase phosgenation plant (100) with the streams in regular operation and which comprises at least (i) an apparatus (1000) for providing a gaseous phosgene stream, (ii) an apparatus (2000) for proving a gaseous amine stream, (iii) a mixing zone (3100) for mixing the streams, (iv) a reaction zone (3200) arranged downstream of the mixing zone (3100), and (v) a reaction stopping zone (4000) arranged downstream of the reaction zone (3200), including the workup section (5000) for to recover and recycle unconverted phosgene.

According to the invention, a gas phase phosgenation plant (100) comprises at least the devices listed above as (i) to (v) (cf. also FIG. 1, which shows the devices of a gas phase phosgenation plant (100) to be used in accordance with the invention, including the workup section which is preferably present and the streams in regular operation).

(i) As apparatus for provision of a gaseous phosgene stream (1000), it is possible in principle to use any apparatus which is known from the prior art and is suitable for the conversion of phosgene to the gas phase. Preferably, the phosgene gas is generated by distillation or partial evaporation in a distillation column, as described in DE 10 2009 032413 A1 in paragraphs [0081] to [0118]. The energy can be supplied in the bottom of the column by any conceivable evaporator, for example a natural circulation evaporator, climbing film evaporator and falling film evaporator. Falling film evaporators are especially preferred.

(ii) As apparatus for provision of a gaseous amine stream (2000), it is possible in principle to use any apparatus which is known from the prior art and is suitable for the conversion of an amine to the gas phase, such as evaporation apparatuses known to those skilled in the art. In a preferred embodiment, the apparatus 2000 comprises a device for evaporation and a device for subsequent superheating of the amine (2). Very particular preference is given to multistage evaporation and superheating systems in which droplet separators are installed between the evaporation and superheating systems and/or the evaporation apparatuses also have the function of a droplet separator. Suitable droplet separators are described, for example, in "Droplet Separation", A. Bürkholz, VCH Verlagsgesellschaft, Weinheim-New York-Basle-Cambridge, 1989. After leaving the last superheater in flow direction, the gaseous reactant stream (20) preheated to its target temperature is fed to the reaction space.

(iii) A mixing zone (3100) usable in accordance with the invention can be constructed in a manner known to those skilled in the art, preferably as described in EP-A-2 196 455, especially in paragraphs [0047] to [0049], and EP-A-1 935 876, especially in paragraphs [0027] to [0029]. The mixing zone begins where, in regular operation, the streams (10) and (20) meet one another for the first time.

(iv) The amine and phosgene gas streams that meet one another for the first time in the mixing zone (3100) are converted further in a delay apparatus, the reaction zone (3200). Mixing zone (3100) and reaction zone (3200) can preferably also be combined in a single apparatus, the reactor (3000), as described in EP 2 196 455 A1, especially in paragraphs [0042] to [0049].

Figure 2:
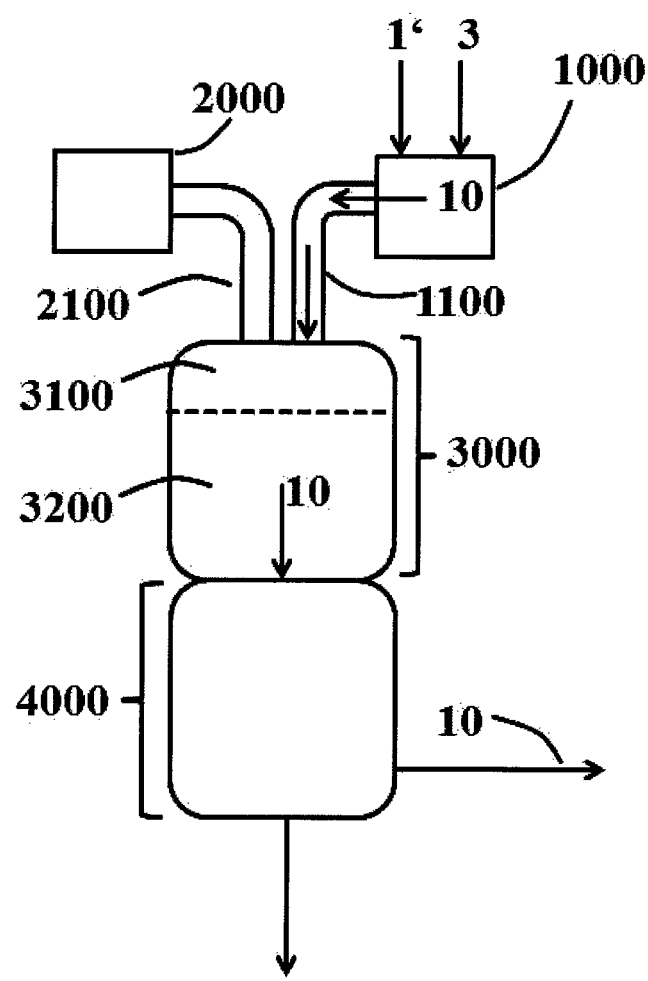
FIG. 2 shows a method according to the invention in which an isocyanate (4) is formed by reacting an amine (2) with a stoichiometric excess of phosgene (1) in relation to the primary amino groups of the amine (2) by which the gas phase phosgenation plant (100) is started up in accordance with step (I).

The devices 1100 and 2100 which connect the apparatuses for provision of the gaseous phosgene gas stream (1000) and amine gas stream (2000) to the mixing zone (3100), in accordance with the invention, are those devices which are suitable for transfer of the respective gas stream (10) or (20) from the apparatuses 1000 and 2000 into the mixing zone (3100). These devices comprise, as well as pipelines for transport of the gas streams, preferably also nozzle apparatuses which assure intensive mixing of phosgene gas stream (10) and amine gas stream (20) in the mixing zone (3100). It is possible to inject each of gas streams (10) and (20) individually into the mixing zone (3100). However, preference is given to an embodiment in which the pipelines of the devices 1100 and 2100 open into a common nozzle apparatus (not shown in FIG. 1). In this embodiment, one of the two gas streams, preferably the amine gas stream (20), is supplied to the mixing zone (3100) via an internal nozzle arranged centrally in a preferably cylindrical vessel. The other gas stream, preferably the phosgene gas stream (10) is introduced via the annular space formed by the outer wall of the inner nozzle and the inner wall of the vessel. The two gas streams mix at the exit orifice of the inner nozzle (=start of the mixing zone). Such an embodiment is shown, for example, in FIG. 1 of EP-A-1 449 826 and in FIG. 1 of EP-A-1 362 847. In this case, the devices 1100 and 2100 are partly integrated into one another and into the mixing zone (3100). It is also possible, as shown in FIG. 2 of EP-A-1 449 826, to use an arrangement composed of several individual nozzles in place of a single central nozzle. Further embodiments usable in accordance with the invention for the devices 1100 and 2100 are described, for example, in EP-A-2 196 455, especially in paragraphs [0047] to [0048], and EP-A-1 935 876, especially in paragraphs [0027] and [0028].

(v) Reaction stopping zones (4000) usable in accordance with the invention are known to those skilled in the art. Preference is given to an embodiment as described in EP 1 935 875 B1, especially in paragraphs [0024] and [0025]. Preferably, the reaction stopping zone is put into operation no later than when stream 20 enters the mixing zone (3100) for the first time in step (III). In the reaction stopping zone (4000), the crude product of the reaction (40) comprising, as well as the isocyanate (4), essentially also the hydrogen chloride coproduct and unconverted phosgene is cooled rapidly, preferably by injecting an inert solvent (preferably ortho-dichlorobenzene, ODB), optionally together with a portion of previously formed and recycled isocyanate (4), into the gas stream (40). Preferably, the crude reaction product (40) is separated in the reaction stopping zone (4000) into a gaseous component (vapor, 50) and a liquid component (60).

In a particularly preferred configuration of the method of the invention, the crude product obtained in the reaction stopping zone (4000) is worked up in the same gas phase phosgenation plant (100) in order to isolate the isocyanate (4) from the liquid mixture (60). In this case, the gas phase phosgenation plant (100) additionally comprises (vi) a workup section (5000).

Suitable apparatuses for workup are described in WO 2011/003532, especially page 5 line 19 to page 28 line 5, and in EP 1 371 636 B1, EP 1 371 635 B1 and EP 1 413 571 B1, the whole document in each case. The workup section (5000) can be divided into devices for recovering and recycling unconverted phosgene (and for removing the hydrogen chloride coproduct) (5100) and devices for obtaining the isocyanate prepared in pure form (and optionally for recycling inert solvent) (5200). The workup section is indicated merely schematically in FIG. 1 without the details given hereinafter. More particularly, the workup section (5000) comprises a scrubbing column (5110) for removing isocyanate from the vapors (50) from the reaction stopping zone (4000) by scrubbing with an inert solvent, a phosgene absorption column (5120) for recovering phosgene from the vapors from the scrubbing column (5110) by absorption in an inert solvent, which results in separation of hydrogen chloride and inerts (70) from the phosgene, a phosgene desorption column (5130) for separation of phosgene and inert solvent, a solvent column (5210), especially for removal of low boilers (especially inert solvent from the reaction stopping zone) from the crude isocyanate, a fine purification column (5220), especially for removal of high boilers (e.g. polyurea-containing residues) from the isocyanate prepurified in the solvent column, such that purified end product is obtained.

It is possible (not shown in FIG. 1) to integrate the apparatus (1000) for provision of a gaseous phosgene stream (10) into the phosgene desorption column (5130) in such a way that the solvent-containing phosgene stream originating from the workup is evaporated together with fresh phosgene (1') and distilled in the phosgene desorption column (5130). The gaseous phosgene obtained is fed to the mixing zone via the device 1100, while the inert solvent removed is preferably conducted into the scrubbing column (5110) and/or the phosgene absorption column (5120).

In step (I) of the method of the invention (see also FIG. 2), in the apparatus 1000, a gaseous phosgene stream (10) is provided and introduced through the device 1100 continuously into the mixing zone (3100), the reaction zone (3200) and the reaction stopping zone (4000), the pressure $p_{10}$ being greater than the pressure $p_{3100}$ in the mixing zone (3100). During this time, the supply of amine gas stream (20) has been stopped. Preferably, during the performance of step (I), the plant sections device 1100, mixing zone (3100), reaction zone (3200) and reaction stopping zone (4000) are free of impurities, especially free of solvent which, in preceding production cycles, may possibly have been distributed in the phosgenation plant as a result of recycled phosgene streams from the stoppage of the reaction or added deliberately as an inert substance. Preferably, the phosgene gas mass flow rate M'(10) is adjusted as early as in step (I) to the later target value $M'_{target}(10)$ during the continuous production at the desired capacity. The gaseous phosgene stream (10) may, as well as phosgene (1), also contain an inert substance (3). In the apparatus 1000, the phosgene gas stream (10) is heated to a temperature $T_{30}$ of 200° C. to 600° C. at an absolute pressure $p_{30}$ of 200 mbar to 3000 mbar. The values for $T_{10}$ and $p_{10}$ relate to the entire stream (10), i.e. if appropriate to the mixture of phosgene (1) and inert substance (3), on exit from the device 1100. Inert substances (3) usable in accordance with the invention are, as well as those substances that are already gaseous at room temperature and standard pressure, such as nitrogen, helium or argon, also the vapors of inert organic solvents that are liquid at room temperature and standard pressure, for example aromatic hydrocarbons, optionally having halogen substitution, for example, chlorobenzene or dichlorobenzene (all isomers, preferably ortho-dichlorobenzene). Particular preference is given to using nitrogen to dilute the phosgene. The proportion of inert substance (3) in the phosgene gas stream (10) may be chosen in the manner customary in the prior art. In step (I), the phosgenation plant (100) is heated up with the phosgene circulation, followed by the buildup of an inert gas flow on the amine side in step (II).

In step (I), the phosgene in the phosgene stream (10) preferably comes at least partly from the workup section of the gas phase phosgenation plant (5000) (recycled phosgene (1") from the preceding production cycle). The recovery of the phosgene in the workup is preferably effected as described in WO 2011/003532, especially page 5 line 19 to page 28 line 5.

Figure 3:
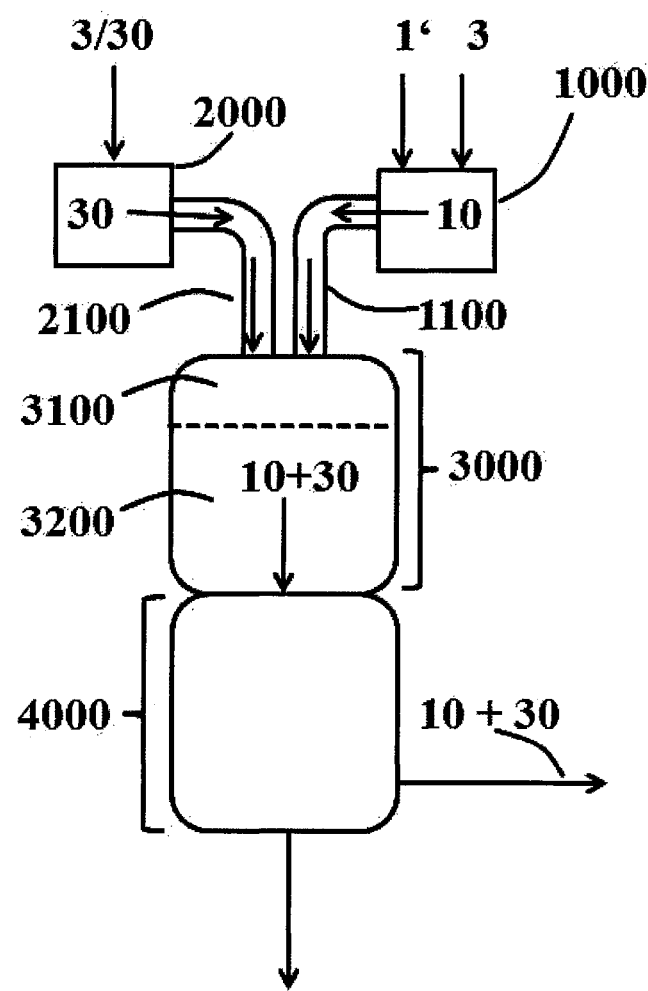
FIG. 3 shows a method according to the invention in which an isocyanate (4) is formed by reacting an amine (2) with a stoichiometric excess of phosgene (1) in relation to the primary amino groups of the amine (2) by which the gas phase phosgenation plant (100) is started up in accordance with step (II).

In step (II) of the method of the invention (see also FIG. 3), an inert gas stream (30) is conducted at least through the device 2100 (and thence through the mixing zone (3100), the reaction zone (3200) and the reaction stopping zone (4000)). Preferably, the apparatus 2000 and the device 2100 are inertized in such a way that an inert gas stream (30) is conducted from the apparatus 2000 into the device 2100 (and thence through the mixing zone (3100), the reaction zone (3200) and the reaction stopping zone (4000)). Any barrier devices present between the apparatus 2000 and the device 2100 (and between the device 2100 and the mixing zone 3100) are open during this step, in order that the inert gas stream (30) can flow out of the evaporation apparatus 2000 into the device 2100 (and thence into the mixing zone (3100)).

The inertization can be accomplished by (a) introducing an inert substance (3), preferably one which is liquid at room temperature and standard pressure, into the apparatus 2000 at a temperature $T_3$<200° C. and heating it therein. This embodiment is advantageous especially when the reaction mixture is diluted during the reaction in regular operation with the vapors of an inert substance (3) which is liquid at room temperature and standard pressure. It is possible to introduce the inert substance (3) in liquid form into the apparatus 2000 and to evaporate it only once therein. Inert substances (3) that are particularly suitable in variant (a) are inert solvents such as aromatic hydrocarbons, optionally having halogen substitution, for example chlorobenzene or dichlorobenzene (all isomers, preferably ortho-dichlorobenzene). In the apparatus 2000, the inert substance (3) is heated (i.e. evaporated in the case of introduction as a liquid) so as to obtain an inert gas stream (30) having a temperature $T_{30}$ of 200° C. to 600° C., preferably 200° C. to 500° C. and more preferably 250° C. to 500° C., and an absolute pressure $p_{30}$ of 100 mbar to 3000 bar, preferably 150 mbar to 2800 mbar and more preferably 200 mbar to 2500 mbar. As a result, the apparatus 2000 and the downstream device 2100 are heated up. The streams (3) and (30) do not differ in terms of chemical composition, but differ merely in terms of temperature and optionally pressure. After the stream (3) introduced into the apparatus 2000 has been heated, it is referred to as stream (30).

It is also possible (b) to provide the inert gas stream (30) outside the apparatus 2000 at a temperature $T_{30}$ of 200° C. to 600° C., preferably 200° C. to 500° C. and more preferably 250° C. to 500° C., and an absolute pressure $p_{30}$ of 100 mbar to 3000 mbar, preferably 150 mbar to 2800 mbar and more preferably 200 mbar to 2500 mbar. This embodiment is advantageous especially when the reaction mixture, during the reaction in regular operation, is being diluted with an inert substance already in gaseous form at room temperature and standard pressure, such as nitrogen, helium or argon. The inert gas stream (30) can be conducted (b.1) into the device 2100 (and thence through the mixing zone (3100), the reaction zone (3200) and the reaction stopping zone (4000)). The inert gas stream (30) can also (b.2) be fed into the apparatus 2000 (and thence through device 2100, the mixing zone (3100), the reaction zone (3200) and the reaction stopping zone (4000)). In variant (b.2), it is also possible to heat up the inert gas stream (30) introduced further in the apparatus 2000 within the scope of the above-defined temperature ranges.

In a preferred embodiment, the inert gas stream (30) consists of the same inert substance (3) which is optionally used to dilute the phosgene (1). Step (II) is conducted simultaneously with or after step (I). If step (II) is conducted after step (I), the phosgene flow rate (10) established in step (I) is maintained during the performance of step (II). The optimal flow rate of inert gas stream (30) to be used is guided by the size of the plant sections to be heated and can be ascertained easily by the person skilled in the art. Step (II) prevents, on commencement of the amine supply in step (III), the apparatus 2100 from containing phosgene, and prevents occurrence of condensation of the amine (2) in the mixing zone (3100) or in the reaction zone (3200).

In step (III) of the method of the invention, in the apparatus 2000, a gaseous amine stream (20) is provided and introduced continuously into the mixing zone (3100) through the device 2100. Preference is given here to maintaining an inert gas stream (30). This is advantageously done by diluting the amine (2) with an inert substance (3) which is either in gaseous form from the outset (i.e. as inert gas stream (30)) or is converted to the gas phase (i.e. to an inert gas stream (30)) together with the amine (2) in the device 2000. In this embodiment, the amine gas stream (20) thus comprises, as well as the amine (2), the inert substance (3) too. In the apparatus 2000, the amine gas stream (20) is heated to a temperature $T_{20}$ of 200° C. to 600° C. at an absolute pressure $p_{20}$ of 100 mbar to 3000 mbar. The values of $T_{20}$ and $p_{20}$ are based on the entire stream (20), i.e. if appropriate on the mixture of amine (2) and inert substance (3), on exit from the device 2100, i.e. in the preferred embodiment with use of a nozzle in the device 2100 at the nozzle mouth. Inert substances (3) usable in accordance with the invention are, as in the case of phosgene, as well as those substances that are already gaseous at room temperature and standard pressure, such as nitrogen, helium or argon, also the vapors of inert organic solvents that are liquid at room temperature and standard pressure, for example aromatic hydrocarbons, optionally having halogen substitution, for example, chlorobenzene or dichlorobenzene (all isomers, preferably ortho-dichlorobenzene). Particular preference is given to using nitrogen to dilute the amine. If both the amine (2) and the phosgene (1) are diluted with an inert substance (3), it is preferable that the inert gas stream (30) used is the same inert substance. This inert substance is preferably nitrogen. The proportion of inert substance (3) in the amine gas stream (10) may be chosen in the manner customary in the prior art. In step (III), the amine (2) is evaporated into the device 2100 permanently purged with an inert gas stream (30), at which point the entire phosgenation plant from reactant streams to product removal has to be ready for operation. At the time of exit of the amine gas stream (20) from the device 2100, in the preferred embodiment with use of a nozzle from the mouth of the amine nozzle, into the mixing zone (3100), a phosgene excess, preferably of at least 150%, has to be assured. The temperature in the device 2100 and in the mixing zone (3100) and the reaction zone (3200) preferably has a value above the dew point of the amine (2). The pressure in the apparatus 2000 (amine evaporation) $p_{20}$ has to be above the pressure $p_{3100}$ in the mixing zone (3100), which is preferably 80 mbar (absolute) to 2500 mbar (absolute). This can be accomplished by first evaporating amine (2) and then, by (possibly further) addition of an inert gas stream (30), adjusting the pressure to the desired value $p_{20}$. It is preferable to choose equal pressures $p_{10}$ and $p_{20}$. The pressure thus chosen has to be greater than the target pressure $p_{3100}$ in the mixing zone (3100), in order that sufficient flow of the gas flows (10) and (20) into the mixing zone (3100) is assured and backmixing into the respective reactant nozzles is reliably ruled out.

According to the invention, the composition and the mass flow rate of stream (20) are matched to the composition and mass flow rate of stream (10) such that, in the mixing zone (3100), phosgene (1) is present in a stoichiometric excess in relation to the primary amino groups of the amine (2). Preferably, the phosgene excess based on the primary amino groups of the amine is 150% to 400% of theory, more preferably 160% to 350% of theory and most preferably 170% to 300% of theory. Theoretically, one mole of phosgene reacts with one mole of amino groups, meaning that two moles of phosgene theoretically react with one mole of a diamine.

The mass flow rate of amine gas stream 20 is increased continuously or in stages, preferably continuously, to a desired target value $M'_{target}(20)$. Preferably, this increase is accomplished in such a way that at least 80% of the desired target value $M'_{target}(20)$ is attained within less than 12 hours, preferably less than 6 hours, more preferably less than 3 hours and most preferably less than 1 hour. This prevents turbulent backmixing of phosgene, amine or phosgene/amine mixture at the point of entry into the mixing zone (3100).

If two or more reaction zones (3200) are to be operated in parallel, it is preferable to start them up successively, as described above. The dimensions of the secondary systems (such as the HCl absorption, phosgene absorption, any solvent workup or else offgas treatment) have to be such that the gaseous coproducts and any by-products obtained (especially the hydrogen chloride coproduct) can be absorbed and processed further in an unproblematic manner in the course of startup.

As soon as the two mass flow rates, M'(10) and M'(20), have attained their respective target values, the gas phase phosgenation plant (100) can be operated further by a method known from the prior art. Preferably, for this purpose, the reaction mixture produced, with avoidance of backmixing, is guided continuously through the reaction zone and converted therein, preferably at a temperature of 200° C. to 600° C. and an absolute pressure of 80 mbar to 2500 mbar within a mean contact time of 0.05 to 15 seconds, in an adiabatic or isothermal manner, preferably in an adiabatic manner, to a gaseous process product comprising the desired isocyanate (4). Suitable embodiments are described in EP 2 196 455 B1 and EP 1 935 876 B1.

In the reaction stopping zone (4000), the gaseous process product (40) exiting from the reaction zone (3200) is cooled rapidly. This is preferably accomplished by contacting with an inert solvent, the temperature of which is kept below the boiling temperature of isocyanate (4) and above the decomposition temperature of the carbamoyl chloride corresponding to the amine converted. Suitable embodiments are described in EP 1 935 875 B1. Any isocyanate (4) not condensed in this step is preferably removed from the gas mixture remaining in the reaction stopping zone by scrubbing with a scrubbing liquid and preferably combined with the condensate (60) obtained in the reaction stopping zone (4000). A suitable embodiment is described in EP 1 935 875 B1, especially in paragraphs [0024] and [0025].

Thereafter, the desired isocyanate (4) is isolated by distillation from the crude liquid process product thus obtained. Suitable embodiments are known to those skilled in the art and are described, for example, in WO 2013/139703, EP 1413 571 B1, EP 1 371 635 B1, EP 1 371 636 B1.

If all the reactant pathways are run up simultaneously, the above-described problems can occur. Phosgene can flow into the device 2100 (preferably amine nozzle) and can lead to blockages, baked-on polyurea, etc. In addition, the amount of phosgene at least briefly goes significantly below the phosgene excess desired at nameplate capacity in continuous production, again giving rise to by-products because the flow equilibria are disrupted and there is uncontrolled mixing. The residence time of the reactants in the reaction space is disrupted when both reactant streams are opened simultaneously.

The procedures of the invention therefore give rise to the following advantages for the startup procedure of a gas phase phosgenation:
i) Avoidance of blockages in the device 2100 (preferably the amine nozzle) and in the mixing zone (3100) and hence avoidance of any requirement for multiple startups because the plant had to be shut down to clean the device 2100 (preferably the amine nozzle).
ii) As a result of (i), saving of energy.
iii) Increasing the productivity of the plant because there is no need for repeated shutdowns and restarts because of the occurrence of baked-on material and deposits.
iv) Increase in plant reliability because the thermal stress on the phosgenation plant (100) is reduced by the decrease in startup operations.
v) Reduced by-product formation and shortened thermal stress on the product, accompanied by an increase in the relative yield.
vi) Avoidance or reduction of precipitates, baked-on material and blockages in the equipment (for example in the apparatus 2000 and the device 2100 or in the reaction zone prior to the stoppage of the reaction), accompanied by prolonging of the onstream time of the process.
vii) Lower level of waste after cleaning of the equipment (for example less polyurea to be removed).
viii) Avoidance of off-spec material which can arise as a result of repeated poor startup and shutdown. Such poor-quality startup material thus does not have to be cut with good-quality polyisocyanate or even in the worst case incinerated.

Thus, the method of the invention enables, through avoidance of backmixing of phosgene (1) into the amine gas stream (20), the startup of a gas phase phosgenation plant and the subsequent workup of the crude isocyanate formed in a technically seamless manner with reduced or, in the ideal case, zero downtime with directly high end product quality.

EXAMPLES

Content figures in ppm or % are parts by mass based on the total mass of the respective substance/stream of matter. General Conditions for the Preparation of TDI with a "Run-in" as Phase Production Plant (100) (i.e. on Completion of Startup)

(See also FIG. 1 (simplified diagram))

TDA (2) is evaporated continuously in an amine evaporator (2000) together with nitrogen (3). The amine gas stream (20) thus obtained, containing 12 t/h of gaseous TDA (2), is injected continuously into the phosgenation reactor (3000) via a conduit (2100) with an amine nozzle present at the end thereof toward the phosgenation reactor (3000). The residence time of the TDA stream (20) from departure from the evaporator (2000) until exit from the amine nozzle is 5 seconds. At the same time, via a phosgene rectifier which is used as disclosed in EP-A-1 362 847, 61 t/h of a gaseous phosgene stream (10) are injected continuously into the phosgenation reactor (3000). The phosgene used is a mixture of fresh phosgene (1') and phosgene (1") recovered in the workup section (5000). In this case, the two reactants are mixed well, and there is no backmixing. The temperature of the gaseous TDA stream (20) at the mouth of the nozzle is 380° C. (TDA has a residence time of about 1 second at this temperature in the feed to the nozzle mouth). The gaseous phosgene (10) has a temperature of 320° C. when it leaves the phosgene rectifier, the residence time of the hot phosgene between the last phosgene superheater and phosgene rectifier being 2 seconds. The gaseous mixture of the streams (10) and (20) has a residence time of 8 seconds in the gas phase reactor (3000) and reacts at an absolute pressure of 1692 mbar to give a gaseous reaction mixture (40). The downstream reaction stopping zone (4000) comprises a two-stage "quench" in which the gaseous reaction mixture (40) is cooled down to 168° C. by spraying in ortho-dichlorobenzene (ODB), such that it is condensed and a mixture (60) of crude TDI and ODB collects in the bottoms vessel (4100). Excess phosgene, hydrogen chloride formed in the reaction and inerts are very substantially degassed from the bottoms vessel (4100) under these conditions, with reduction of the entrainment of TDI by means of internals. This residual process gas stream (50) is worked up (5100) to recover entrained TDI, phosgene and hydrogen chloride, as described in WO 2011/003532, page 11 lines 24 to 25. The mixture (60) from the bottoms vessel (4100) is worked up (5200) as described in EP 1 413 571 B1, giving TDI (4) in a mass flow rate of 15.6 t/h.

TDI (4) prepared in this way typically has a purity of >99.97% (gas chromatography, GC), a residual solvent content of ODB of <5 ppm (GC), a residual chlorine content of hydrolyzable chloride of <10 ppm (titration in accordance with ASTM D4663), an acidity of bound chlorine of <5 ppm (titration in accordance with ASTM D5629), and the color number, measured as the Hazen number, is <15 (determined in accordance with DIN EN ISO 6271).

Comparative Example 1: Startup of a Gas Phase Phosgenation Plant (100) with Feeding of Amine (2) Before Phosgene (1)

A gas phase phosgenation plant (100) is operated as described above. After a shutdown, the plant is restarted as follows: The amine evaporator (2000) and the conduit (2100) including the amine nozzle are charged with a nitrogen gas stream (30), with a set temperature of 380° C. The phosgenation reactor (3000) is reactant- and product-free and is inertized with hot nitrogen (30). The amine evaporation in the amine evaporator (2000) is started, and TDA is evaporated at 300° C., heated to 410° C. in a further heat exchanger and injected as gaseous TDA (20) at an absolute pressure of 1683 mbar through the amine nozzle into the phosgenation reactor (3000). The amount of TDA (2) which is introduced into the phosgenation reactor (3000) during a planned startup period of 45 minutes is to be increased continuously from 0 t/h to 12 t/h. 5 minutes after commencement of the amine supply, a phosgene gas stream (10) is injected into the phosgenation reactor (3000) at a mass flow rate of 61 t/h, a temperature of 320° C. and an absolute pressure of 1683 mbar at the reactor inlet. After 20 minutes, the plant had to be shut down because the pressure differential between entry of the TDA gas stream (20) and phosgene gas stream (10) reactants into the phosgenation reactor (3000) and vapor gas outlet from the bottom (4100) had risen rapidly to more than 1000 mbar, rather than 10 mbar in normal operation, and the evaporation energy required to evaporate phosgene (1) and TDA (2) can no longer be raised. The startup is terminated by shutting down the phosgene and TDA supply. After the phosgenation plant has been opened, a demister blocked with TDA and polyureas in the bottom (4100) and surfaces covered with deposits over a large area in the quenches (4000) are found.

Comparative Example 2: Startup of a Gas Phase Phosgenation Plant (100) with Simultaneous Feeding of Amine (2) and Phosgene (1)

A gas phase phosgenation plant (100) is operated as described above. After a shutdown, the plant is restarted as follows: The amine evaporator (2000) and the conduit (2100) including the amine nozzle are charged with a nitrogen gas stream (30), with a set temperature of 380° C. The phosgenation reactor (3000) is reactant- and product-free and is inertized with hot nitrogen (30). The amine evaporation in the amine evaporator (2000) is started, and TDA is evaporated at 300° C., heated to 410° C. in a further heat exchanger and injected as gaseous TDA (20) at an absolute pressure of 1683 mbar through the amine nozzle into the phosgenation reactor (3000). The amount of TDA (2) which is introduced into the phosgenation reactor (3000) during a planned startup period of 45 minutes is to be increased continuously from 0 t/h to 12 t/h. Simultaneously with the passage of the TDA gas stream (20) through the amine nozzle into the phosgenation reactor (3000), the phosgene supply is opened and the phosgene gas stream (10) is injected into the phosgenation reactor (3000) with a mass flow rate of 61 t/h, a temperature of 320° C. and an absolute pressure of 1691 mbar at the reactor inlet. The plant can be operated in the normal mode of operation after a startup time of 45 minutes. After 5 days, the plant had to be shut down because the pressure differential between entry of the TDA gas stream (20) and phosgene gas stream (10) reactants into the phosgenation reactor (3000) and vapor gas outlet from the bottom (4100) had risen to 793 mbar, rather than 10 mbar in normal operation, and the evaporation energy required to evaporate phosgene (1) and TDA (2) can barely be raised. After shutdown and opening of the plant, severe polyurea-containing deposits are found at the mouth of the amine nozzle, along the surface of the reactor space and on the surfaces of the quenches.

Comparative Example 3: Startup of a Gas Phase Phosgenation Plant (100) with Feeding of Phosgene (1) Before Amine (2), but without Inertization of the Amine Feed Devices with an Inert Gas Stream (30)

Circulation of phosgene is built up by running recycled phosgene (1") from the workup (5100) of the vapors (50) from the reaction stopping zone (4000) at a temperature of 320° C. through the phosgenation reactor (3000), the reaction stopping zone (4000), back to the workup. In the reaction stopping zone (4000), during this time, only the second quench in flow direction of the reaction mixture (40) is in operation, as a result of which the phosgene stream is cooled down. In this phosgene circuit, 61 t/h of phosgene are circulated (step (I)). During this time, the amine evaporator (2000) and the conduit 2100 including the amine nozzle are not purged with a nitrogen gas stream (30). As soon as the phosgenation reactor (3000) has been heated to 320° C., the amine evaporation is started—without the conduit (2100) including the amine nozzle being purged with a nitrogen gas stream (30) beforehand—by running liquid TDA (2) preheated to 220° C. together with nitrogen into the amine evaporator (2000), evaporating it therein with the aid of a heat exchanger at 300° C. and then heating it to 410° C. with a further heat exchanger. The TDA stream (20) thus obtained is injected at an absolute pressure of 1654 mbar through the amine nozzle into the phosgenation reactor (3000) (step (III)). The amount of TDA (2) which is introduced into the phosgenation reactor (3000) during the startup of the gas phase phosgenation plant (i.e. until the amine mass flow rate reaches $M'_{target}(2)$, which happens after 45 minutes) is increased continuously from 0 t/h to 12 t/h, the operating pressure in the phosgenation reactor (3000) at the end of the startup being 1641 mbar (absolute). The first quench in flow direction of the reaction mixture (40) is put into operation shortly before TDA gas stream (20) for the first time leaves the amine nozzle in the direction of the phosgenation reactor (3000) in the course of startup. The phosgene consumed after the startup of the plant is replaced by a mixture of fresh phosgene (1') and phosgene recovered in the workup (1"). After 60 minutes, 15.6 t/h of TDI (4) leave the last distillation column of the workup stage.

After the startup, the pressure differential between amine evaporation (2000) and the phosgenation reactor (3000) increases ever further. After 3 hours, the phosgenation reactor (3000) has to be shut down because the operating pressure at the amine nozzle has risen to 2.5 bar (absolute). After shutdown and opening of the plant, charred residues are found in the exit orifice of the amine nozzle and in the pipeline leading to the amine nozzle. This is attributable to backflows of phosgene into the device 2100 during the startup phase, forming TDI deposits which block the exit orifice of the amine nozzle.

Example 4 (Inventive)

The procedure is as described in example 3, except that, as soon as the phosgenation reactor (3000) has been heated to 320° C., the amine evaporator (2000) and the conduit (2100) including the amine nozzle are purged with hot nitrogen (30), with a set temperature of 380° C. (step (II)).

After 60 minutes, 15.6 t/h of TDI (4) leave the last distillation column of the workup (5200).

In this procedure, the blocking of the amine nozzle and the formation of deposits in the phosgenation reactor (3000) during the startup phase are prevented, such that the plant (100) can be run over a long period of up to more than one year. The formation of unwanted by-products such as polyureas etc. is significantly reduced, and later blending of the startup material with TDI of higher purity can be omitted.

The invention claimed is:

1. A method of operating a gas phase phosgenation plant that is configured to produce an isocyanate (4) by reacting an amine with phosgene and that comprises at least
   (i) an apparatus for providing a gaseous phosgene stream,
   (ii) an apparatus for providing a gaseous amine stream,
   (iii) a mixing zone for mixing the gaseous phosgene stream and the gaseous amine stream, with the mixing zone being connected by connecting devices for the phosgene stream and for the amine stream to the apparatus for providing a gaseous phosgene stream and the apparatus for providing a gaseous amine stream,
   (iv) a reaction zone arranged downstream of the mixing zone for further conversion of the previously mixed streams,
   (v) a reaction stopping zone arranged downstream of the reaction zone to end the reaction,
   and optionally
   (vi) a workup section which comprises devices for recovery and recycling of unconverted phosgene and devices for obtaining the isocyanate prepared in pure form,
   wherein the gas phase phosgenation plant is started up by:
   (I) providing a gaseous phosgene stream at a temperature $T_{10}$ of 200° C. to 600° C. with an absolute pressure $p_{10}$ of 100 mbar to 3000 mbar in the apparatus for providing a gaseous phosgene stream and continuously introducing this gaseous phosgene stream through the connecting device for the phosgene stream into the mixing zone, the reaction zone and the reaction stopping zone, the pressure $p_{10}$ being greater than the pressure $p_{3100}$ in the mixing zone;
   (II) either simultaneously with or after step (I),
      (a) introducing an inert substance, at a temperature $T_3 < 200°$ C. into the apparatus for providing a gaseous amine stream, heating the inert substance in the apparatus for providing a gaseous amine stream to obtain an inert gas stream and passing said inert gas stream through the connecting device for the amine stream, the mixing zone, the reaction zone and the reaction stopping zone
      or
      (b) introducing an inert gas stream
         (b.1) into the connecting device for the amine stream and thence through the mixing zone, the reaction zone and the reaction stopping zone
         or
         (b.2) into the apparatus for providing a gaseous amine stream and thence through the connecting device for the amine stream, the mixing zone, the reaction zone and the reaction stopping zone,
      where the inert gas stream in variant (a) and in variant (b) has a temperature of 200° C. to 600° C. and an absolute pressure $p_{30}$ of 100 mbar to 3000 mbar,
      and
      where the pressure $p_{30}$ in variant (a) and in variant (b) is greater than the pressure $p_{3100}$ in the mixing zone;
   and
   (III) after (II), providing a gaseous amine stream at a temperature $T_{20}$ of 200° C. to 600° C. with an absolute pressure $p_{20}$ of 100 mbar to 3000 mbar in the apparatus for providing a gaseous amine stream and continuously introducing this gaseous amine stream through the connecting device for the amine stream into the mixing zone, where the pressure $p_{20}$ is greater than the pressure $p_{3100}$ in the mixing zone, and where the composition and the mass flow rate of the gaseous amine stream are matched to the composition and the mass flow rate of the gaseous phosgene stream such that, in the mixing zone, phosgene is present in a stoichiometric excess in relation to the primary amino groups of the amine.

2. The method as claimed in claim 1, in which the gas phase phosgenation plant includes the workup section and in which, in the regular operation of the gas phase phosgenation plant, the phosgene in the phosgene gas stream comprises a mixture of fresh phosgene and recycled phosgene recovered in the recovery and recycling devices.

3. The method as claimed in claim 1, in which the phosgene in the phosgene gas stream from (I) consists at least partly of recycled phosgene.

4. The method as claimed in claim 1, in which the compositions and mass flow rates of streams of gaseous phosgene and of gaseous amine are matched to one another such that, in (III), in the mixing zone, phosgene is present in a stoichiometric excess in relation to the primary amino groups of the amine in an amount that is at least 150% of the theoretically required amount.

5. The method as claimed in claim 1, in which the pressures $p_{10}$ and $p_{20}$ are the same.

6. The method as claimed in claim 1, in which the mass flow rate of gaseous amine stream is increased continuously or in stages, to a desired target value $M'_{target}$.

7. The method as claimed in claim 6, in which the mass flow rate of gaseous amine stream is increased such that at least 80% of the desired target value $M'_{target}$ is attained within not more than 12 hours.

8. The method as claimed in claim 1, in which the absolute pressure $p_{3100}$ is adjusted to a value of 80 mbar to 2500 mbar.

9. The method as claimed in claim 1, in which the connecting device for the phosgene stream comprises a nozzle.

10. The method as claimed in claim 1, in which the connecting device for the amine stream comprises a nozzle.

11. The method as claimed in claim 1, in which the connecting devices for the phosgene stream and for the amine stream comprise a common nozzle apparatus.

12. The method as claimed in claim 1, in which the inert gas stream is maintained during the performance of (III).

13. The method as claimed in claim 1, in which the reaction stopping zone is operated below the boiling temperature of the isocyanate and above the breakdown temperature of the carbamoyl chloride which corresponds to the amine by contacting the gaseous process product exiting from the reaction zone with an inert solvent.

14. The method as claimed in claim 13, in which the reaction stopping zone is put into operation no later than when the gaseous amine stream enters the mixing zone for the first time in (III).

15. The method as claimed in claim 1, in which the amine is selected from the group consisting of isophoronediamine, hexamethylenediamine, bis(p-aminocyclohexyl)methane, tolylenediamine and diphenylmethanediamine.

16. The method as claimed in claim 1, in which said inert substance introduced in (II) (a) is liquid at room temperature and standard pressure.

\* \* \* \* \*